United States Patent [19]

Tellier et al.

[11] 3,956,282
[45] May 11, 1976

[54] METHOD FOR PREPARING AZINES

[76] Inventors: Pierre Tellier, 35, Boulevard Emile Z0la, 69 Oullins; Henri Mathais, 31, Boulevard Baron du Marais, 69, Ste.-Foy-les-Lyon; Jean-Pierre Schirmann, 4, Avenue de la Gare, 69 Brignais; Francis Weiss, 3, Chemin du Perron, 69 Pierre Benite, all of France

[22] Filed: Mar. 13, 1973

[21] Appl. No.: 340,763

[30] Foreign Application Priority Data

Mar. 16, 1972 France .............................. 72.09134

[52] U.S. Cl. ........................ 260/240 G; 260/345.1; 260/345.9; 260/465 E; 260/465.5 R; 260/566 B
[51] Int. Cl.$^2$ ...................................... C07C 119/00
[58] Field of Search ................. 260/566 B, 465.5 R, 260/465 E, 345.1, 345.9, 240 G

[56] References Cited
UNITED STATES PATENTS 2,870,206    1/1959    Meyer et al. .................... 260/566 B

*Primary Examiner*—Gerald A. Schwartz

[57] ABSTRACT

A method is disclosed for preparing symmetrical azines of the formulas $$\begin{array}{c}R^1\\ \diagdown\\ R^2\end{array}C=N-N=C\begin{array}{c}R^1\\ \diagup\\ R^2\end{array} \quad (I)$$

$$\begin{array}{c}R^1\\ \diagdown\\ R^3\end{array}C=N-N=C\begin{array}{c}R^1\\ \diagup\\ R^3\end{array} \quad (II)$$

$$\begin{array}{c}R^3\\ \diagdown\\ R^4\end{array}C=N-N=C\begin{array}{c}R^3\\ \diagup\\ R^4\end{array} \quad (III)$$

and unsymmetrical azines of the formulas $$\begin{array}{c}R^1\\ \diagdown\\ R^2\end{array}C=N-N=C\begin{array}{c}R^1\\ \diagup\\ R^3\end{array} \quad (IV)$$

$$\begin{array}{c}R^1\\ \diagdown\\ R^2\end{array}C=N-N=C\begin{array}{c}R^3\\ \diagup\\ R^4\end{array} \quad (V)$$

and mixtures of azines (I), (II) and (IV) and (I), (III) and (V), wherein $R^1$, $R^2$, $R^3$ and $R^4$ each is a hydrogen atom, a straight chain alkyl radical of from 1 to 12 carbon atoms, a branched chain alkyl radical or unsubstituted or alkyl substituted cycloalkyl radical of from 3 to 12 carbon atoms, a hydrocarbon radical of from 6 to 12 carbon atoms containing an aromatic nucleus; further provided that $R^1$ and $R^2$ can be the same or different radicals, and $R^3$ and $R^4$ are the same or different radicals and each are different from $R^1$ and $R^2$; or $R^1$ and $R^2$ or $R^1$ and $R^3$ or $R^3$ and $R^4$ bonded to the same carbon atom together form an unsubstituted or aliphatic substituted alkylene radical of from 3 to 11 carbon atoms, each of the aforesaid radicals being unsubstituted or substituted with one or more radicals which are stable in the medium in which the azines are produced.

The method comprises reacting ammonia and a carbonyl compound of the formula $$R^1-\underset{\underset{O}{\|}}{C}-R^2 \quad (VI)$$

alone or together with a different carbonyl compound $$R^1-\underset{\underset{O}{\|}}{C}-R^3 \quad (VII)$$

or $$R^3-\underset{\underset{O}{\|}}{C}-R^4 \quad (VIII)$$

wherein $R^1$, $R^2$, $R^3$ and $R^4$ each have the same meaning defined above with hydrogen peroxide in the presence of a carboxylic ester to provide the azine or mixture of azines.

4 Claims, No Drawings

METHOD FOR PREPARING AZINES

BACKGROUND OF THE INVENTION

1. Field of the Invention

This invention relates to a method for preparing symmetrical azines as well as mixtures containing symmetrical and unsymmetrical azines.

2. Description of the Prior Art

Aldehydes are known to react with ammonia in a complex manner giving rise to various addition, condensation or polymerization products (see for example, *The Chemistry of the Carbon-Nitrogen Bond*, S. Patai, Interscience, London, 1970, page 67) or with hydrogen peroxide to form unstable peroxide products and to provide peroxide products upon reaction with ammonia and hydrogen peroxide (see for example, *J. Chem. Soc.* 1969, C, p. 2678).

Moreover, it is known that ammonia, a ketone and hydrogen peroxide react together to produce aminoperoxides (see for example, *J. Chem. Soc.* 1969, C, p. 2663) and in the presence of tungstic or molybdic acid as catalyst, can lead to formation of an oxime (see for example, *J. Gen. Chem. (U.S.S.R.)* 1960, 30 p. 1635).

A method for preparing azines comprising the oxidation of ammonia in the presence of a ketone or aldehyde by means of an oxidizing medium of hydrogen peroxide and cyanogen or a nitrile, the latter being converted to the corresponding amide during the reaction, is fully disclosed in commonly assigned pending U.S. application Ser. No. 152,413, filed June 11, 1971.

Still another method for preparing azines comprises reacting ammonia, a carbonyl compound and hydrogen peroxide under appropriate conditions in the presence of a catalytic quantity of certain salts. This method is fully disclosed in commonly assigned pending U.S. application Ser. No. 267,921, filed June 30, 1972.

SUMMARY OF THE INVENTION

It has been surprisingly discovered that symmetrical azines of the formulas

(I)

(II)

(III)

and unsymmetrical azines of the formulas

(IV)

(V)

and mixtures of azines (I), (II) and (IV) and (I), (III) and (V), wherein $R^1$, $R^2$, $R^3$ and $R^4$ each is a hydrogen atom, a straight chain alkyl radical of from 1 to 12 carbon atoms, a branched chain alkyl radical or unsubstituted or alkyl substituted cycloalkyl radical of from 3 to 12 carbon atoms, a hydrocarbon radical of from 6 to 12 carbon atoms containing an aromatic nucleus; further provided that $R^1$ and $R^2$ can be the same or different radicals, and $R^3$ and $R^4$ are the same or different radicals and each are different from $R^1$ and $R^2$; or $R^1$ and $R^2$ or $R^1$ and $R^3$ or $R^3$ and $R^4$ bonded to the same carbon atom together form an unsubstituted or aliphatic substituted alkylene radical of from 3 to 11 carbon atoms, each of the aforesaid radicals being unsubstituted or substituted with one or more radicals which are stable in the medium in which the azines are produced can be prepared in good yield by reacting ammonia and a carbonyl compound of the formula

(VI)

alone or together with a different carbonyl compound

(VII)

or

(VIII)

wherein $R^1$, $R^2$, $R^3$ and $R^4$ each have the same meaning defined above with hydrogen peroxide in the presence of a carboxylic ester to provide the azine or mixture of azines.

When a single carbonyl compound (VI) is reacted according to the method of this invention, a symmetrical azine having the formula

(I)

is produced.

When, for example, both $R^1$ and $R^2$ of carbonyl compound (VI) is hydrogen, the carbonyl compound is formaldehyde and the azine resulting from this method is the symmetrical aldazine, formaldazine, which has the formula $$CH_2 = N - N = CH_2$$

When only one of the substituents is hydrogen, the resulting aldazine, for example, has the formula

wherein the substituent $R^1$ is not hydrogen.

When neither of the substituents of the carbonyl compound (VI) is hydrogen, the carbonyl compound (VI) is a ketone and the resulting azine is a symmetrical ketazine of the formula

(I)

wherein none of the substituents $R^1$ and $R^2$ is hydrogen.

When in addition to carbonyl compound (VI), a different carbonyl compound (VII) is simultaneously reacted according to the method of this invention, a mixture of symmetrical and unsymmetrical azines of the formulas

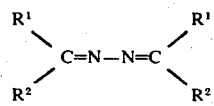 (I)

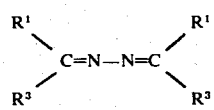 (II)

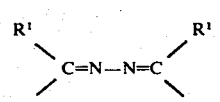 (IV)

is produced.

And if in addition to carbonyl compound (VI), a different carbonyl compound (VIII) is simultaneously reacted according to the method of this invention, a mixture of symmetrical and unsymmetrical azines of the formulas

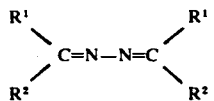 (I)

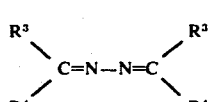 (III)

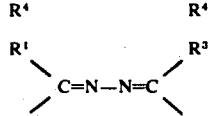 (V)

is produced.

When both carbonyl compounds (VI) and (VII) are aldehydes, a mixture of symmetrical and unsymmetrical aldazines will be obtained. Similarly, if both carbonyl compounds (VI) and (VII) or (VI) and (VIII) are ketones, a mixture of symmetrical and unsymmetrical ketazines will be produced. And if one of the carbonyl compounds (VI), (VII) or (VIII) is an aldehyde and the other carbonyl compound which is being simultaneously reacted is a ketone, the method of this invention will yield a mixture of azines containing a symmetrical aldazine, a symmetrical ketazine and an unsymmetrical azine possessing the characteristics of both an aldazine and a ketazine.

Any number of different aldehydes and/or ketones may be reacted according to the method of this invention to yield mixtures of azines, the number and amount of which are present in the mixture being made to depend upon the number, amount and nature of the carbonyl compounds reacted.

DESCRIPTION OF THE PREFERRED EMBODIMENTS

The reaction mechanism whereby ammonia, carbonyl compounds, hydrogen peroxide and percarboxylic ester are converted to azines according to this invention is not yet fully understood. In this reaction, the carboxylic ester has been found to be converted to the corresponding ammonium salt with the liberation of alcohol. Representing as exemplary of the carboxylic esters which can advantageously be used herein, compounds of the general formula

 (IX)

the reaction can be theorized to proceed as follows:

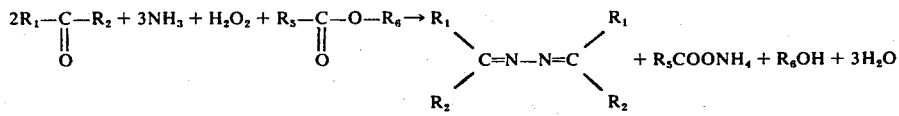

The esters

 (IX)

which can be employed in the method of this application can be monofunctional carboxylic esters derived from the alcohols $R_6$—OH wherein $R_6$ represents a straight chain, branched chain or cyclic hydrocarbon radical of up to about 12 carbon atoms or the phenols $R_6$—OH wherein $R_6$ represents a phenyl group, and a monocarboxylic acid $R_6COOH$ wherein $R_5$ is a straight chain, branched chain, cyclic or aromatic radical having up to about 12 carbon atoms.

The useful esters herein can also be polyfunctional carboxylic esters derived from the alkanols or phenols $R_6$—OH and the polycarboxylic acids $R'_5(COOH)_n$ wherein $n$ is a whole number between 2 and 6 and $R'_5$ is a simple linkage in which case $n$ is 2, or a straight chain, branched chain, cyclic or aromatic radical of valence n having up to about 12 carbon atoms.

The useful esters herein can also be polyfunctional carboxylic esters derived from the monocarboxylic acids $R_5COOH$ and the polyhydroxy alkanols or polyhydroxy phenols $R'_6$—$(OH)_m$ wherein $m$ is a whole number from 2 to 6 and $R'_6$ is an aliphatic or aromatic hydrocarbon radical of valence m having up to about 12 carbon atoms.

The terminal groups of the carboxylic esters which can be employed in the method of this invention can also be joined together to form a straight or branched divalent hydrocarbon radical of from about 2 to 11 carbon atoms, which is to say, lactones. Lactones having ring of from 4 to 12 members as well as their cyclic or acyclic oligomers are useful herein. The radicals $R_5$, $R'_5$, $R_6$ and $R'_6$ can contain up to six ethylenic bonds or substituents such as chlorine, bromine or fluorine atoms and nitro, alkoxy, hydroxy or carboxylic acid groups.

Examples of carboxylic esters which can advantageously be used in the method of this invention include the formates, acetates, monochloroacetates, trichloroacetates, trifluoroacetates, propionates, butyrates, isobutyrates, valerates, hexanoates, octanoates, nonanoates, dodecanoates, banzoates, ortho, meta and para chlorobenzoates, p-methoxybenzoates, p-nitrobenzoates, oxalates, malonates, succinates, glutarates, adipates, pimelates, butane1,2,4-tricarboxylates, o-phthalates, isophthalates, terephthalates, trimellitates, pyromellitates, β-hydroxypropionates, tartrates and citrates of the following alcohols or phenols: methanol, ethanol, n-proponal, isopropanol, n-butanol, isobutanol, 2-butanol, tertiary butanol, the amyl alcohols, n-hexanol, n-heptanol, n-octanol, 2-ethylhexanol, n-dodecanol, cyclohexanol the methylcyclohexanols, allylic alcohol, crotylic alcohol, Δ-3-tetrahydrobenzylic alcohol, benzylic alcohol, 2-methoxyethanol, 3-methoxy propanol, 2-ethoxyethanol, 3-ethoxyisopropanol, ethylene glycol, propylene glycol, 1,3-propanediol, 1-buten-3, 4-diol, 2-buten-1, 4-diol, 2-methylenyl-1,3-propanediol, glycerol, 1,2,3,4-butane tetrol, 1,1,1-trimethylol ethane, 1,1,1-trimethylol propane, pentaerythritol, sorbitol, Δ-3-1,1-dimethylol cyclohexane, phenol, the mono and dichlorophenols, the mononitrophenols, the monoethoxyphenols, the cresols, pyrocatechol, resorcinol and hydroquinone. Examples of lactones which can advantageously be employed include β-propiolactone, γ-butyrolactone, δ-valerolactone and ε-caprolactone.

For convenience and economy, it is advantageous to employ the esters of low molecular weight, especially, the lower alkyl formates in which the alkyl group possesses less than 6 carbon atoms.

The carbonyl compounds of this invention can contain ethylenic bonds and such substituents as chlorine, bromine or fluorine atoms and nitro, hydroxy, alkoxy, carboxylic acid, carboxylic amide or ester and nitrile groups.

Some examples of aldehydes conforming to formulas (VI), (VII) or (VIII) which can be advantageously employed in the method of this invention include formaldehyde, acetaldehyde, propionaldehyde, butyraldehyde, isobutyraldehyde, n-pentanal, pivalaldehyde, oenanthal, 2-ethylhexanal, 3-Δ tetrahydrobenzaldehyde, hexahydrobenzaldehyde, 5-norbornene-2-carboxaldehyde, tetrahydropyran-2-carboxaldehyde, benzaldehyde, the monochlorobenzaldehydes, p-nitrobenzaldehyde, β-chloropropionaldehyde, β-methoxyproprionaldehyde and 4-cyano-2,2,-dimethylbutyraldehyde.

Some examples of ketones conforming to formula (VI), (VII) or (VIII) which can be advantageously employed in the method of this invention include acetone, 2-butanone, 2-pentanone, 3-pentanone, methylisopropylketone, methylisobutylketone, ethylamylketone, methylcyclohexylketone, acetophenone, benzophenone, cyclobutanone, cyclopentanone, cyclohexanone, 2-methylcyclohexanone, 3-methylcyclohexanone, 4-methylcyclohexanone, 2,4-dimethylcyclohexanone, 3,3,5-trimethylcyclohexanone, cycloheptanone, cyclooctanone, cyclodecanone and cyclododecanone.

The reaction components are reacted in the liquid phase and mixed in order or in various combinations. For example, the reaction components can be separately or simultaneously introduced into the reactor on a continuous or batch-wise basis. Thus, the hydrogen peroxide can be added to a mixture of ammonia, carbonyl compound and carboxylic ester; the ammonia or ammonia solution can be added to a mixture of hydrogen peroxide, carbonyl compound and carboxylic ester; the carboxylic ester can be added to a mixture of ammonia, hydrogen peroxide and carbonyl compounds; or one can prepare in advance a mixture of hydrogen peroxide and carbonyl compound to provide a mixture containing one or several known peroxides of the carbonyl compound and react this mixture with ammonia and carboxylic ester. It is advantageous to employ a solvent or blend of solvents to maintain a homogenous reaction medium or to provide at least partial solubilization of the reactants. Examples of solvents which can advantageously be used for this purpose include the saturated alcohols having 1 to 6 carbon atoms such as methanol, ethanol, n-propanol, isopropanol, n-butanol, 2-butanol, isobutanol, tert-butanol, the amyl alcohols and cyclohexanol.

The temperature of the reaction can be varied over a wide range and is advantageously from about −20° to 100°C. The reaction can be carried out at or above atmospheric pressure, at a pressure of up to 10 atmospheres if such is necessary to maintain the reaction components in solution.

The reaction components can be employed in stoichiometric quantities according to the aforedescribed reaction sequence but it is also possible to use other proportions and employ one or more of the reactants in up to a ten-fold excess of the theoretical quantity. It is generally advantageous not to employ an excess of hydrogen peroxide by comparison to the other reactants in order to avoid or minimize secondary decomposition reaction of this reagent or undesirable oxidation products.

It can be advantageous to add one or more known and conventional stabilizers for peroxidic compounds which exercise a buffering action on the pH of the reaction medium. For example, from about 0.1 to 1.0% by weight of the reaction medium of phosphoric acid, pyrophosphoric acid, citric acid, nitrilotriacetic acid, ethylenediaminetetraacetic acid or the alkaline metal or ammonium salts of the aforesaid acids can be used. Upon completion of the reaction, the azines can be recovered from the medium by means of known and conventional techniques including extraction with a non-miscible solvent, fractional distillation or a combination of these two methods.

The azines of this invention are useful as intermediates in the preparation of many important products and in particular are useful for preparing hydrazine and hydrazine salts by hydrolysis according to known and conventional methods. Hydrolysis of the azines releases the carbonyl compounds which can be recycled for preparing additional quantities of azines according to the method of this invention.

The following examples are illustrative of the method of this invention. Although the examples employ but a single carbonyl compound resulting in symmetrical azines it is understood that the same procedures can be followed except that two or more different aldehydes or ketones or one or more aldehydes and ketones are reacted to result in a mixture of symmetrical and unsymmetrical azines as hereinbefore described.

EXAMPLE 1

A solution of 14.5 gm of acetone (0.25 moles), 5 gm water, 65 gm methanol, 4.9 gm of a 70% by weight aqueous solution of hydrogen peroxide (0.1 moles) and 0.25 gm of the disodium salt of ethylene diaminetetraacetic acid (EDTA) were placed in a reactor and thereafter 5.1 gm ammonia (0.3 moles) were added. The reaction medium was heated to 40°C and over a period of 10 minutes, 6 gm of methyl formate (0.1 moles) were then added. The medium was maintained at 40°C for 3½ hours then at 50°C for 2 hours. The quantity of acetoneazine contained in the medium was then determined by chemical analysis and gas phase chromatography. 8.2 gm of acetoneazine (0.073 moles) corresponding to a yield of 73% based on the total amount of the hydrogen peroxide used had formed.

EXAMPLE 2

Repeating substantially the same conditions as in EXAMPLE 1 except that the methanol was replaced with an equal weight of water, after the reaction medium had reacted for 3 hours at 40°C, analysis indicated that 6.1 gm of acetoneazine (0.054 moles) corresponding to 54% of the theoretical yield based on the total amount of hydrogen peroxide used had formed.

EXAMPLE 3

Repeating substantially the same conditions as in EXAMPLE 1 except that the acetone was replaced with an equivalent amount of 2-butanone (18 gm; 0.25 moles), after the reaction medium had reacted for 3½ hours at 40°C, analysis indicated that 9.5 gm of the azine of 2-butanone (0.068 moles) corresponding to 68% of the theoretical yield based on the hydrogen peroxide used had formed.

EXAMPLE 4

Repeating substantially the same conditions as EXAMPLE 1 except that the acetone was replaced with an equivalent quantity of cyclohexanone (24.5 gm; 0.25 moles), after the reaction medium had reacted for 3½ hours at 40°C, analysis indicated that 4.4 gm of cyclohexanoneazine (0.023 moles) corresponding to 23% of the theoretical yield based on the hydrogen peroxide used had formed.

EXAMPLE 5

Repeating substantially the same conditions as in EXAMPLE 1 except that the methyl formate was replaced with a corresponding quantity of n-propyl formate (8.8 gm; 0.1 moles) and the reaction was conducted at 20°C, after 7 hours at this temperature, analysis showed there to be 5.6 gm of acetoneazine (0.050 moles) present or 50% of the theoretical yield based on the hydrogen peroxide used. By increasing the temperature to 50°C and maintaining the medium at this temperature for another 2½ hours, the reaction continued and the yield of acetoneazine reached 62% of the theoretical amount.

EXAMPLE 6

Substantially the same reaction conditions as set forth in EXAMPLE 1 were repeated except that the methyl formate was replaced with a corresponding quantity of phenyl benzoate (19.8 gm; 0.1 moles) which was introduced into the mixture containing the other reaction components over a period of three minutes at 20°C. After reacting for 3 hours at this temperature, the ammonium benzoate precipitate which had formed was removed from the medium by filtration and analysis of the filtrate showed there to be 6.4 gm of acetoneazine (0.057 moles) present, thus corresponding to 57% of the theoretical yield based on the amount of hydrogen peroxide used.

EXAMPLE 7

Repeating substantially the same reaction conditions as in EXAMPLE 1 except that the methyl formate was replaced with 11.4 gm of ε-caprolactone (0.1 moles) which was introduced into the reaction medium containing the other reactants over 10 minutes at 20°C, after the reaction medium had reacted for 3 hours at this temperature, analysis showed there to be 0.8 gm of acetoneazine (0.007 moles) present thus corresponding to 7% of the theoretical yield based on the amount of hydrogen peroxide used.

EXAMPLE 8

Repeating substantially the same reaction conditions as in EXAMPLE 1 except that the methyl formate was replaced with 7.05 gm of β-propriolactone (0.098 moles) which was introduced into the reaction medium containing the other reactants over 10 minutes at 40°C, after the reaction medium had reacted for 1 hour at this temperature, analysis showed there to be 6.7 gm of acetoneazine (0.060 moles) present thus corresponding to 60% of the theoretical yield based on the amount of hydrogen peroxide used.

EXAMPLE 9

Repeating substantially the same reaction conditions as in EXAMPLE 1 except that the methyl formate was replaced with 8.6 gm of γ-butyrolactone (0.1 moles) which was introduced into the reaction medium containing the other reactants over 10 minutes at 40°C, after the reaction medium had reacted for 5 hours at this temperature, analysis showed there to be 6.7 gm of acetoneazine (0.60 moles) present thus corresponding to 60% of the theoretical yield based on the amount of hydrogen peroxide used.

EXAMPLE 10

Repeating substantially the same reaction conditions as in EXAMPLE 1 except that the methyl formate was replaced with 11.8 gm of ethyl lactate (0.1 moles) which was introduced into the reaction medium containing the other reactants over 10 minutes at 50°C, after the reaction medium had reacted for 7 hours at this temperature analysis showed there to be 2.46 gm of acetoneazine (0.022 moles) present thus corresponding to 22% of the theoretical yield based on the amount of hydrogen peroxide used.

EXAMPLE 11

Repeating substantially the same reaction conditions as in EXAMPLE 1 except that the methyl formate was replaced with 12.9 gm of ethylmonochloroacetate (0.10 moles) which was introduced into the reaction medium containing the other reactants over 10 minutes at 50°C, after the reaction medium had reacted for 4½ hours at this temperature, analysis showed there to be 4.9 gm of acetoneazine (0.0436 moles) present thus corresponding to 43.6% of the theoretical yield based on the amount of hydrogen peroxide used.

EXAMPLE 12

Repeating substantially the same reaction conditions as in EXAMPLE 1 except that the methyl formate was replaced with 22.8 gm of butyl maleate (0.1 moles) which was introduced into the reaction medium containing the other reactants over 10 minutes at 50°C, after the reaction medium had reacted for 8 hours at this temperature, analysis showed there to be 1.56 gm of acetone azine (0.014 moles) present thus corresponding to 14% of the theoretical yield based on the amount of hydrogen peroxide used.

We claim:

1. A method for preparing azines which consists of reacting
   a. ammonia;
   b. a carbonyl compound selected from formaldehyde, acetaldehyde, propionaldehyde, butyraldehyde, isobutyraldehyde, n-pentanal, pivalaldehyde, oenanthal, 2-ethylhexanal, 3-Δ-tetrahydrobenzaldehyde, hexahydrobenzaldehyde, 5-norbornene-2-carboxaldehyde, tetrahydropyran-2-carboxaldehyde, benzaldehyde, a monochlorobenzaldehyde, p-nitrobenzaldehyde, β-chloropropionaldehyde, β-methoxypropionaldehyde, 4-cyano-2,2-dimethylbutyraldehyde, acetone, 2-butanone, 2-pentanone, 3-pentanone, methylisopropylketone, methylisobutylketone, ethylamylketone, methylcyclohexylketone, acetophenone, benzophenone, cyclobutanone, cyclopentanone, cyclohexanone, a methylcyclohexanone, 2,4-dimethylcyclohexanone, 3,3,5-trimethylcyclohexanone, cycloheptanone, cyclooctanone, cyclodecanone and cyclododecanone, and mixtures thereof;
   c. hydrogen peroxide; and
   d. a carboxylic ester selected from β-propiolactone, γ-butyrolactone, σ-valerolactone, ε-caprolactone and the formates, acetates, monochloroacetates, trichloroacetates, trifluoroacetates, propionates, butyrates, isobutyrates, valerates, hexanoates, octanoates, nonanoates, dodecanoates, benzoates, chlorobenzoates, p-methoxybenzoates, p-nitrobenzoates, oxalates, malonates, succinates, glutarates, adipates, pimelates, butane-1,2,4-tricarboxylates, o-phthalates, isophthalates, terephthalates, trimellitates, pyromellitates, β-hydroxypropionates, tartrates and citrates of methanol, ethanol, n-propanol, isopropanol, n-butanol, isobutanol, 2-butanol, tertiary butanol, an amyl alcohol, n-hexanol, n-heptanol, n-octanol, 2-ethylhexanol, n-dodecanol, cyclohexanol, a methcyclohexanol, allylic alcohol, crotylic alcohol, Δ-3-tetrahydrobenzylic alcohol, benzylic alcohol, 2-methoxyethanol, 3-methoxy propanol, 2-ethoxyethanol, 3-ethoxyisopropanol, ethylene glycol, propylene glycol, 1,3-propanediol, 1-buten-3,4-diol, 2-buten-1,4-diol, 2-methylenyl-1,3-propanediol, glycerol, 1,2,3,4-butane tetrol, 1,1,1-trimethylol ethane, 1,1,1-trimethylol propane, pentaerythritol, sorbitol, Δ-3-1,1-dimethyol cyclohexane, phenol, mono and dichlorophenols, a mononitrophenol, a monoethoxyphenol, a cresol, pyrocatechol, resorcinol and hydroquinone, and recovering the azine or mixture of azines from the reaction medium.

2. The method of claim 1 wherein the reaction is carried out in the presence of a solvent comprising a saturated alcohol of from 1 to 6 carbon atoms.

3. The method of claim 1 wherein the reaction is carried out at a temperature between about −20° and 100°C.

4. The method of claim 1 wherein one or more of the reaction components is used in the stoichiometric amount up to about a ten-fold excess.

* * * * *

UNITED STATES PATENT AND TRADEMARK OFFICE
CERTIFICATE OF CORRECTION

PATENT NO. : 3,956,282
DATED : May 11, 1976
INVENTOR(S) : Pierre Tellier, et al.

It is certified that error appears in the above-identified patent and that said Letters Patent are hereby corrected as shown below:

Column 4, Lines 9-10
reads "percarboxylic", should read --carboxylic--

Column 4, Line 43
reads "$R_6COOH$", should read --$R_5COOH$--

Column 5, Line 8
reads "banzoates", should read --benzoates--

Column 5, Lines 52-53
reads "4-cyano-2,2,-dimethylbutyraldehyde",
should read --4-cyano-2,2-dimethylbutyraldehyde--

Column 6, Line 37
reads "reaction", should read --reactions--

Column 10, Line 13
reads "methcyclohexanol", should read --methylcyclohexanol--

Signed and Sealed this

Thirty-first Day of August 1976

[SEAL]

Attest:

RUTH C. MASON
Attesting Officer

C. MARSHALL DANN
Commissioner of Patents and Trademarks